United States Patent [19]

Kasafirek et al.

[11] Patent Number: 5,182,285

[45] Date of Patent: * Jan. 26, 1993

[54] CELL-PROTECTIVE COMPOSITION FOR PREVENTING OR TREATING OF PEPTIC ULCER

[75] Inventors: Evžen Kasafírek; Václav Plaisner; Libuše Korbová; Jiřj Kohout; Jiřina Čizková; Ivan Krejčí; Arnošt Pospišil; Milan Pešak; Antonín Šturc; Jiří Křepelka; Antonín Dlabač, all of Praha; Jiří Vanzura, Hradec Králové, all of Czechoslovakia

[73] Assignee: Spojene Podniky Pro Zdravotnickou Vyrobu, Praha, Czechoslovakia

[*] Notice: The portion of the term of this patent subsequent to Aug. 26, 2008 has been disclaimed.

[21] Appl. No.: 507,087

[22] Filed: Apr. 6, 1990

Related U.S. Application Data

[63] Continuation of Ser. No. 355,839, May 17, 1989, abandoned, which is a continuation of Ser. No. 118,506, Nov. 9, 1987, abandoned.

[30] Foreign Application Priority Data

Nov. 7, 1986 [CS] Czechoslovakia ............ PV 8061-86

[51] Int. Cl.$^5$ ............................................. A61K 31/495
[52] U.S. Cl. .................................. 514/255; 544/231
[58] Field of Search ................ 514/249, 255; 544/231

[56] References Cited

U.S. PATENT DOCUMENTS 3,928,357 12/1975 Ramey et al. ...................... 544/231

FOREIGN PATENT DOCUMENTS 2127807 4/1984 United Kingdom .

OTHER PUBLICATIONS

Kasafirek et al. II, Chemical Abstracts, vol. 100, No. 192289d (1984).
Bantam Medical Dictionary, Bantam Books, publishers, p. 350 (1982).

Primary Examiner—Mukund J. Shah
Assistant Examiner—E. Bernhardt
Attorney, Agent, or Firm—Thomas A. Gallagher; Michael G. Marinangeli

[57] ABSTRACT

A cell-protective composition for preventing or treating of a peptic ulcer due to topical endogenous lesion of gastric or duodenal mucous membrane comprises as a physiologically active component the cyclo-(1-alanyl-amino-1-cyclopentanecarbonyl)cyclodipeptide. The subject composition is designated for administration by oral or parenteral route. It is substantially non-toxic and well tolerated, and acts beneficially, even at low dosage level.

1 Claim, No Drawings

CELL-PROTECTIVE COMPOSITION FOR PREVENTING OR TREATING OF PEPTIC ULCER

This application is a continuation of Ser. No. 118,506, filed Nov. 9, 1987 also now abandoned.

FIELD OF THE INVENTION

The invention relates to a cell-protective composition for preventing and/or treating endogenous lesions of cells and tissues, especially those of the gastric or duodenal mucous membrane. The subject composition is designated for administration by oral or parenteral route; it has only slight toxicity, is well tolerated and acts beneficially even at low dosage level.

DESCRIPTION OF PRIOR ART

The invention provides for a cell-protective composition for preventing and/or treating endogenous lesions of cells and tissues, especially those of the gastric or duodenal mucous membrane. The subject composition comprises as the physiologically active component a specific spirocyclic dipeptide, cyclo(1-alanyl-1-amino-1-cyclopentanecarbonyl). This peptide compound was originally developed and tested by the inventors' team in SPOFA corporate research in connection with an extensive study of new spirocyclic dipeptides and their action on the central nervous system. The aforenamed compound and a structurally defined series of related analogs are the subject of patent protection here and abroad. More specifically, they are described by U.S. Pat. application No. 538,096, presently abandoned and refiled as a continuation-in-part application No. 915,834. The parent application relates to novel biologically active 2,5-piperazinedione derivatives (resulting from cyclization of the corresponding dipeptides) and to a method for the preparation thereof, and also to pharmaceutical compositions comprising t hose physiologically active compounds. These compounds were originally found to produce valuable specific effects on the central nervous system of mammals.

The 2, 5-piperazinedione derivatives of the preceding application evidence surprising biological effects, particularly on the memory of animals. This was shown using the respective standard pharmacological tests, so-called "conditioned response" and "passive avoidance response" duration tests. Similar activity was previously observed by others in the MSH-inhibiting factor (melano-stimulating hormone—ie. MIF, melanostatin). This substance, however, must be administered parentally, preferably by subcutaneous route, since upon oral administration, it undergoes rapid enzymatic inactivation in the gastrointestinal tract. Contrary to this natural agent, the aforementioned cyclo(1-alanyl-1-amino-1-cyclopentanecarbonyl) compound of the preceding invention, highly potent in the passive avoidance test when administered s.c., either immediately after use or 30 minutes prior to the retention, also evidences similar activity on oral administration of doses of the same order of magnitude, and its effects is protracted over a time period of many hours. Further pharmacological assays also revealed that the compound inhibits the development of tolerance to the cataleptic effect after repeated administration of neuroleptics. In the standard experimental model that is used for approximating the development of tardive dyskinesias, oral administration of the compound significantly inhibited the tolerance after isofloxythepin, the long acting neuroleptic drug.

The compound, administered p.o., also significantly inhibits the decrease of the homovanillic acid content in the corpus striatum of rats and prevents the development of supersensitivity of the dopaminergic receptors in the same tissue. Accordingly, this agent can be expected to have an anti-dyskinetic effect. The MSH-inhibiting factor (MIF, melanostatin) is active under experimental conditions only after subcutaneous administration. As explained in the preceding patent application and its C.I.P. successor, the subject 2, 5-piperazinedione derivatives, even on oral administration, exert their action mostly at an equal or higher potency level as compared with that of melanostatin, and their effect subsists over a prolonged time period. These derivatives are useful primarily in the treatment of memory disturbances, tardive dyskinesias and Parkinson disease.

It has recently been found that the aforementioned compound surprisingly stimulates the growth of eubiotic, healthy diploid cells from lungs. This remarkable, unexpected observation cannot have been anticipated on the basis of previously reported findings. The present discovery evidences that the presently claimed compound also has a protective and/or regenerating effect on cells and tissues damaged by endogenous physiologic factors, e.g. those eliciting the formation of lesions of gastric or duodenal mucous membrane.

SUMMARY OF THE INVENTION

Said cell-protective composition comprises, as a physiologically active component, a specific spirocyclic dipeptide, cyclo-(1-alanyl-1-amino-1-cyclopentanecarbonyl) of formula I:

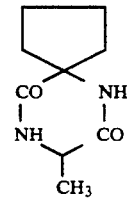

This specific spirocyclic dipeptide is optionally combined with a physiologically inert vehicle (carrier substrate) and if required an adjuvant antacid, topically pain-relieving, spasmolytic and/or sedative component. One of suitable adjuvant agents is represented by oxyphgenone (a nonproprietary generic name), i.e. 2-ethyl-aminoethyl alpha-phenyl-alpha-cyclohexylglycolate, a potent spasmolytic and parasympatolytic (anticholoinergic) pharmaceutical. This can be used either as such, as the base, or preferably in the form of an acid addition salt thereof, e.g. hydrobromide.

The aforenamed spirocyclic dipeptide of formula I is already known (see Czechoslovak Authors' Certificate 231,227 and corresponding British patent No. 2,127,807, French patent no. 83 15599 and Swiss patent No. 655,929). It was originally developed and tested in connection with an experimental study of new spirocycli dipeptides and their effect on the central nervous system. Now it has been found that this compound significantly stimulates the growth of aubiotic, healthy diploid cells from lungs. This remarkable, unexpected observation shows that compound I has a protective and/or regenerating effect on cells and tissues damaged under the action of endogenous factors, e.g. as a result of certain irritative factors that elicit lesions of the gastric or duodenal mucous membrane. Compound I proved to be substantially nontoxic and free of undesired adverse side effects. It beneficial action on said lesions was confirmed by pharmacological tests in vivo, on experimental ulcus disease models, e.g. those induced in animals by the ligature of pylorus (method of Shay) or by i.m. administration of reserpin, whereas negative results (without pronounced improvement) were obtained on ulcus models after indomethacin or kebuzone (ketophenylbutzaone ), i.e. 4-( 3- oxobutyl)- 1,2 -diphenyl-pyrazolidine-3, 5-dione. This indicates that compound I has not a distinctly beneficial effect on ulcus disease induced by improper use of antirheumatic drugs. The experiments were conducted in male Wistar rats having a weight of from 200 to 250 g.

1. Pylorus ligature model

The rats under test were allowed to starve (kept without food) for a period of 24 hours, under ad libitum (nonrestricted) water supply. Compound I was dissolved in isotonic saline and administered intramuscularly at three dosage levels, ie. in doses of 1 mg, 2 mg or 3 mg per animal, immediately on effecting the ligature. After 18 hours the animals were killed and evaluated. The results are summarized in Table 1 (see the attached tables).

As shown by the tabulated data, an i.m. 2 mg. dose of compound I elicited a decrease in the average ulcus size and count by 72%. The reported decrease is highly significant (Student t-test, p lower than 0.001). On the contrary, no substantial differences in the gastric juice quantity, acidity and enzymic activity were observed, which suggests probably low incidence of adverse side effects or digestive dysfunction during the therapy.

2. Reserpin model

The experimental ulcus was induced by intramuscular administration of reserpin (10 mg) to rats kept without food for 24 hours. The results are summarized in Table 2 (see the attached tables). The tabulated data indicate that the same i.m. 2 mg. dose of compound I elicited highly significant decrease in the reserpin ulcus size and count. The observed decrease in proteolytic activity was moderate to slight, changes in proteins and hexoses were clearly insignificant.

The subject compound of formula I can be administered, in accordance with the kind and extent of the treated lesion, either parenterally (by injections) or orally, by ingestion of any convenient oral dispensing form (tablets, coated tablets, capsules, suspensions and the like). The administration route, medical dosage unit and dosage schedule are tailored individually, depending on the nature and severity of the disease and tolerance of the patient. Usual dosage involves 3 to 6 tablets of 10 mg daily QD (on each day) until disappearance of symptoms or according to x-ray examination findings. For rapid mastering of acute lesions it is advisable, at least during the initial stage of the treatment, to prefer parenteral route of administration, at an approximate dosage level of three times a day 5 mg doses in the form of e.g. 5 ml injections. After achieving desired introductory improvement, this parenteral therapy is conveniently replaced by the aforementioned oral treatment. This may be continued, thanks to substantial nontoxicity and very good tolerance of the subject agent, over a prolonged time period, if required for several weeks to several months.

DETAILED EXAMPLES

Further particulars of the subject composition and preferable procedures for its formulation are illustrated by the subsequent nonlimitative examples.

| Example 1 - Injections | |
| --- | --- |
| Compound of formula I | 0.100 g |
| Mannitol | 4.800 g |
| Water for injections | ad 100.0 ml |

Compound I and mannitol are successively dissolved in water for injections and the solution is sterilized by filtration and aseptically filled into ampoules of 5 ml. volume. The obtained injections, when storaged in cold and dark, are stable for at least one year.

| Example 2 - Tablets (direct tableting) | |
| --- | --- |
| Compound of formula I | 10.00 g |
| Calcium hydrogen phosphate dihydrate | 154.60 g |
| Maize starch | 32.50 g |
| Magnesium stearate | 1.90 g |

Compound I is successively mixed with maize starch, calcium hydrogenphosphate and magnesium stearate. The obtained powdery mixture is thoroughly homogenized and directly tableted on a rotary tableting machine to give tablet cores of 7 mm diameter and 190 mg weight. The resulting cores are optionally coated with a polymeric film-forming material, e.g. hydroxypropylmethylcellulose, or a sugar solution.

| Example 3 - Tablets (via granulation) | |
| --- | --- |
| Compound of formula I | 10.00 g |
| Microcrystalline cellulose | 7.00 g |
| Lactose | 86.80 g |
| Maize starch | 42.00 g |
| Sodium carboxymethyl starch | 2.80 g |
| Magnesium stearate | 1.40 g |

Compound I is successively mixed with lactose and portion (36.4 g) of maize starch and homogenized. The homogenizate is granulated with the use of the remaining amount (5.6 g) of maize starch in the form of 12.5% hydrogel. The so formed wet granulation is dried at a temperature of 50° C., the dry material is passed through a sieve (1×1 mm sieve mesh), the remaining solids (Microcrystalline cellulose, sodium carboxymethyl starch and magnesium stearate are added and the mixture is homogenized and tableted on a rotary tableting machine to give tablet cores of 7 mm diameter and 150 mg weight. If required, the core surface is coated as described in the preceding Example 2.

| Example 4 - Tablets (via granulation with polyvinylpyrrolidone) | |
| --- | --- |
| Compound of formula I | 10.00 g |
| Calcium hydrogenphosphate dihydrate | 20.00 g |
| Lactose | 102.00 g |
| Maize starch | 20.00 g |
| Polyvinylpyrrolidone | 3.20 g |
| Sodium carboxymethyl starch | 3.20 g |
| Magnesium stearate | 1.60 g |

Compound I is mixed with calcium hydrogenphosphate, lactose and maize starch. The powdery mixture is homogenized, granulated with the use of polyvinylpyrrolidone in the form of its 15% aqueous solution and the obtained granulation is dried and sieved as described in the preceding Example 3. The remaining solids (sodium carboxymethyl starch and magnesium stearate) are admixed and the material is processed as above to tablets of 7 mm diameter and 160 mg weight.

| Example 5 - Composite tablets (via granulation) | |
|---|---|
| Compound of formula I | 10.00 g |
| Oxyphenone hydrobromide | 2.00 g |
| Calcium hydrogenphosphate dihydrate | 152.60 g |
| Maize starch | 32.50 g |
| Magnesium stearate | 1.90 g |

Compound I is successively mixed with oxyphenone hydrobromide, calcium hydrogenphosphate dihydrate and maize starch, the mixture is granulated as described in Example 3, magnesium stearate is admixed and the material is processed as above to tablets of 7 mm diameter and 150 mg weight.

| Example 6 | |
|---|---|
| Compound of formula I | 10.00 g |
| Magnesium trisilicate | 100.00 g |
| Colloidal aluminum phosphate | 400.00 g |
| Lactose | 48.00 g |
| Polyvinylpyrrolidone | 12.00 g |
| Sodium carboxymethyl starch | 18.00 g |
| Magnesium stearate | 12.00 g |

The formulation procedure is similar as described herein before in Example 4 with the only exception that tablet cores of 600 mg weight are prepared.

| Example 7 | |
|---|---|
| Compound of formula I | 10.00 g |
| Diazepam (7-chloro-1, 3-dihydro-1-methyl-5-phenyl-2H-1, 4-benzo-diazepin-2-one) | 2.00 g |
| Calcium hydrogenphosphate dihydrate | 152.00 g |
| Maize starch | 32.50 g |
| Magnesium stearate | 1.90 g |

Compound I is very with diazepam and the above excipients and the powderly mixture is processed to tablet cores substantially by the direct tableting procedure of Example 2.

Although the invention is described and illustrated with reference to a plurality of embodiments thereof, it is to be expressly understood that it is in no way limited to the disclosure of such preferred embodiments but is capable of numerous modifications within the scope of the appended claims.

TABLE 1

| Dosage | Points[a] (average) | Gastric juice volume, ml | HCl mmoles (ml) | Amylase[b] |
|---|---|---|---|---|
| Control | 38 | 14.8 | 0.87 | 0.33 |
| 1 mg | 45 | 12.6 | 0.67 | 0.31 |
| 2 mg | 11 | 14.9 | 0.92 | 0.32 |
| 3 mg | 30 | 16.1 | 1.05 | 0.42 |

Notes:
[a] ulcus response evaluation system according to Vokac et al., Csl. Gastroenterol. Vyz. 11, 22, 1957.
[b] determined by the orcinol method (Amer. Rev. Tuberc. 68, 594, 1952)

TABLE 2

| Dose | Points[a] (average) | Proteases[b] | Proteins[c] | Hexoses[d] |
|---|---|---|---|---|
| Control C1 | 33 | 0.32 | 25 | 0.45 |
| C2 | 11 | 0.25 | 27 | 0.46 |
| 2 mg | 3.8 | 0.24 | 28 | 0.51 |

Notes:
[a] Vokac et al., l.c. (cf. Table 1, note a))
[b] mmoles/g of tissue, J. Gen. Physiol. 16, 59, 1932
[c] mg/g of tissue, Lowery et al., J. Biol. Chem. 193, 265 1951
[d] mg/g of tissue, Amer. Rev. Tuberc. 68, 594, 1952

We claim:
1. A method for preventing or treating a peptic ulcer in a warm-blooded animal, which comprises administering to said animal an effective amount of a physiologically active component, cyclo-(1-alanyl-1-amino-1-cyclopentanecarbonyl) of formula I:

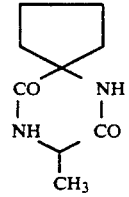

and an inert non-toxic pharmaceutically acceptable carrier.

* * * * *